United States Patent [19]

Outwater et al.

[11] Patent Number: 4,662,730
[45] Date of Patent: May 5, 1987

[54] SCANNING KERATOMETERS

[75] Inventors: Chris Outwater, Los Angeles; Alan Robinson, El Monte, both of Calif.

[73] Assignee: Kerascan, Inc., Santa Ana, Calif.

[21] Appl. No.: 663,469

[22] Filed: Oct. 18, 1984

[51] Int. Cl.$^4$ .................................................. A61B 3/10
[52] U.S. Cl. ..................................... 351/212; 351/247
[58] Field of Search ................................ 351/212, 247

[56] References Cited

U.S. PATENT DOCUMENTS

| 3,453,437 | 7/1969 | Westheimer et al. | 351/212 |
| 4,159,867 | 7/1979 | Achatz | 351/212 |
| 4,407,572 | 10/1983 | Humphrey | 351/212 |

OTHER PUBLICATIONS

Close, Handbook of Optical Holography, 1979, pp. 573-575.

Primary Examiner—Rodney B. Bovernick
Attorney, Agent, or Firm—Blakely, Sokoloff, Taylor & Zafman

[57] ABSTRACT

A scanning keratometer for the rapid and accurate measurement and mapping of the corneal curvature is disclosed. The keratometer has a monochromatic light source directing light to a scanner, preferably controlled by a microcomputer. The scanner directs the light to a holographic element functioning as a lens which in turn focuses the light to a fixed focal point forward of the holographic element independent of the area of the holographic element being illuminated. The subject's eye is position with respect to the fixed focal point so that a part of the light incident to the eye is reflected from the surface thereof again passing through the holographic element, to be deflected from the main optical axis of the system to a suitable area sensor. Assuming the subject's eye is properly positioned and the cornea surface matches the shape of an ideal cornea, the light incident to the cornea will be reflected in the same direction as the incident light, ultimately impinging on the center of the sensor. If, on the other hand, the local area of the cornea being illuminated is not matching, the light reflected from the cornea will be at an angle with respect to the incident light, ultimately impinging on the sensor at a position dependent upon the shape of the local area of the cornea then being illuminated. Various methods of eye positioning, scanning and other aspects of the system are disclosed.

19 Claims, 2 Drawing Figures

SCANNING KERATOMETERS

BACKGROUND OF THE INVENTION

1. Field of the Invention

The present invention relates to the field of keratometers, and more particularly, to the field of scanning keratometers.

2. Prior Art

There are various instances in which a precise mapping of the surface of the human eye is desirable. These can range from simple diagnostic examinations to precise measurements for custom fitting contact lenses, to pre and post surgical cornea mapping.

Several techniques are currently being used for measuring the surface of the eye. The most common technique used in the majority of clinical applications is the standard keratometer. Concentric circles of known diameters (pitch) are projected onto the surface of the eye. The reflected patterns are then studied and compared for any nonconcentricity in the reflections. The shapes however, are sampled a limited number of times, usually with less than ten points being taken and documented. These points are sometimes taken manually, and at other times taken automatically as in the Humphrey automated keratometer. Nevertheless, due to the low number of samples, the measurement is by necessity low in resolution, incurring the imprecision of needed extrapolation from point to point. Thus choosing a contact lens is similar to choosing a pair of shoes. The customer receives a general overall fit, and hopes that any inaccuracies are absorbed in the system. If the proper fit is not accomplished, then the patient must suffer through the discomfort of poorly fitting lenses.

The Humphrey automated keratometer is disclosed in U.S. Pat. Nos. 4,407,572 and 4,420,228. Other patents disclosing keratometers include U.S. Pat. Nos. 3,781,096; 4,019,813; 4,157,859; 4,159,867; 4,429,960; and 4,440,477.

BRIEF SUMMARY OF THE INVENTION

A scanning keratometer for the rapid and accurate measurement and mapping of the corneal curvature is disclosed. The keratometer has a monochromatic light source directing light to a scanner, preferably controlled by a microcomputer. The scanner directs the light to a holographic element functioning as a lens, which in turn focuses the light to a fixed focal point forward of the holographic element, independent of the area of the holographic element being illuminated. The subject's eye is positioned with respect to the fixed focal point so that a part of the light incident to the eye is reflected from the surface thereof, again passing through the holographic element, to be deflected from the main optical axis of the system to a suitable area sensor. Assuming the subject's eye is properly positioned and the cornea surface matches the shape of an ideal cornea, the light incident to the cornea will be reflected along the line of the incident light, ultimately impinging on the center of the sensor. If, on the other hand, the local area of the cornea being illuminated is not matching, the light reflected from the cornea will be at an angle with respect to the incident light, ultimately impinging on the sensor at a position dependent upon the shape of the local area of the cornea then being illuminated. Various methods of eye and apparatus positioning, scanning and other aspects of the system are disclosed.

DETAILED DESCRIPTION OF THE INVENTION

Figure 1:
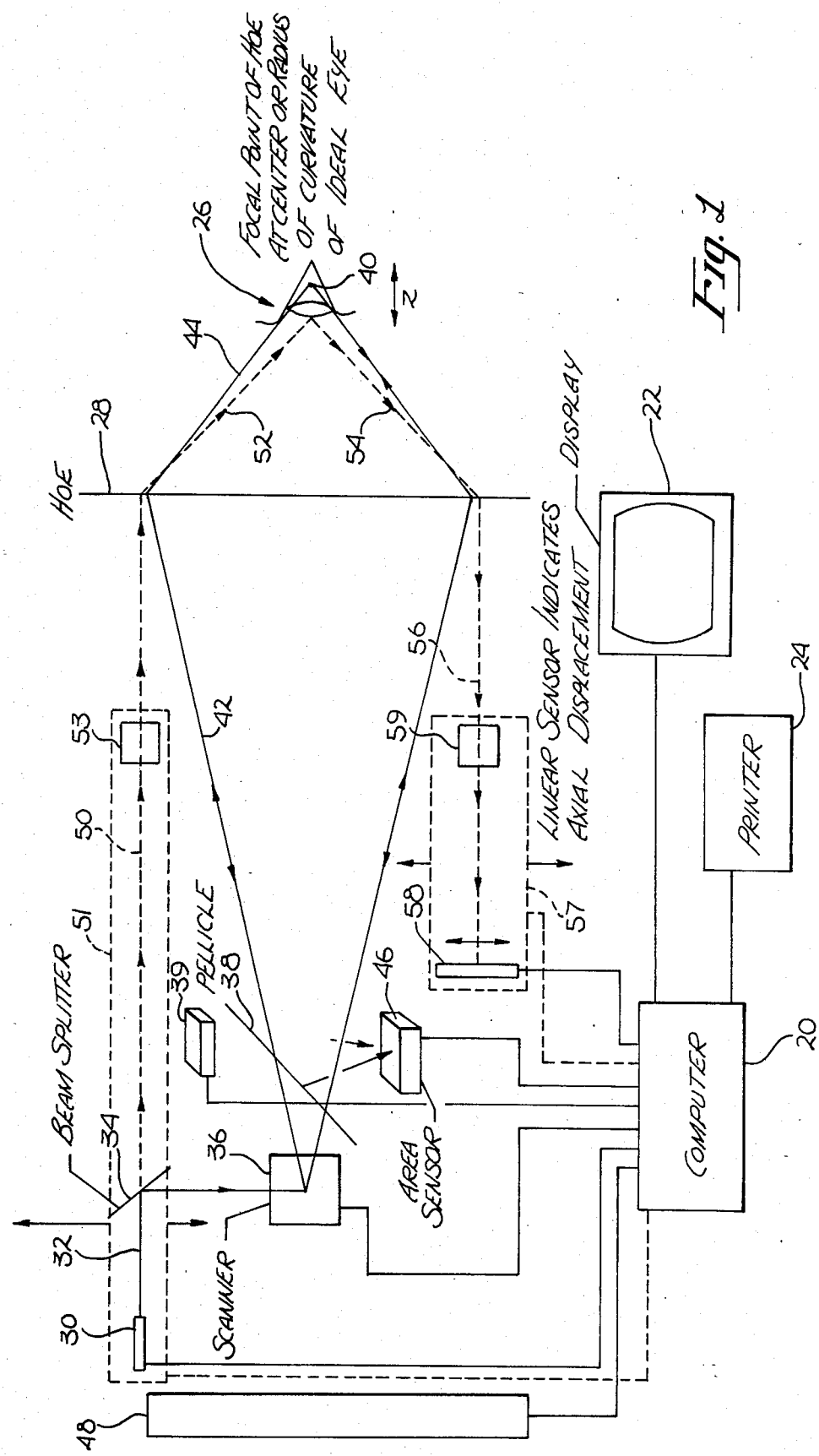
FIG. 1 is a block diagram illustrating a preferred embodiment of the present invention scanning keratometer.

Referring now to FIG. 1, a block diagram of the system of the present invention may be seen. The system of this embodiment is comprised of seven major elements, some of which are coupled to and/or controlled by a small microcomputer such as, by way of example, an IBM PC, with a display 22 for the display of data and control information and a printer 24 for providing a hard copy of the results. At the front of this system, for positioning in front of the patient's eye 26, is a holographic element 28 serving as a lens in a manner to be described. Positioned behind the holographic element is a source 30 of substantially monochromatic light, in the preferred embodiment a helium neon (HeNe) laser coupled to and controlled by the computer 20. The laser 30 directs light in a beam along an optical axis 32, a portion of which light is reflected by a beam splitter 34, to be incident upon a scanner 36, also controlled by computer 20 to controllably deflect the beam incident thereto through a second beam splitter 38 to any part of the holographic element 28 desired. A portion of the beam directed toward the holographic element is deflected by another beam splitter 38 to an area sensor 39, coupled to the computer, which provides a measurement of the X,Y beam position to the computer at all times.

The holographic element 28 acts as a lens, focusing light originating from source 30 and reflected by beam splitter 34 and scanner 36 through beam splitter 38 to any part of the holographic element, onto a fixed focal point 40, ideally coinciding with the center of radius of curvature of the eye being examined. Neglecting for the moment the problem of accurately positioning the patient so that the center of the eye being examined is accurately positioned with respect to the focal point 40 of the holographic element, the operation of the system is as follows. The HeNe laser produces a red beam of monochromatic light at 632.8 nanometers, which beam is reflected in part to the scanner 36 by beam splitter 34. The scanner 36, in turn being coupled to computer 20, is caused to direct the beam in some predetermined scanning pattern on the holographic element 28. In that regard, as shall subsequently be seen, various types of scanners 36 may be used, some of which may be controlled by computer 20, while others may be of a self-scanning type, providing some signal to computer 20 to provide the computer with instantaneous scan position information, either through the sensor 39 or some other means directly coupled to the scanner.

In any event, the beam projected from the scanner onto any operative area of the holographic element will be focused toward the focal point 40 forward of the holographic element, being incident to a portion of the cornea dependent upon the instantaneous scan position. If the eye being examined is perfectly positioned and the cornea surface is perfectly spherical, a portion of the beam will be directly reflected along a line containing the incident beam. Thus, by way of example, if the scanner directs a beam along line 42 at any particular instant, the holographic element 28 will redirect that beam along line 44 to the cornea of the eye being examined. A perfectly spherical cornea, perfectly positioned, will reflect a portion of that incident beam along line 44, the holographic element in turn focusing the reflected beam back along line 42 toward the scanner 36. The beam splitter 38 in turn reflects part of the light reflected from the surface of the cornea to an area sensor 46, which provides electrical output signals to the computer 20 indicative of the position by the reflected beam on the area sensor. Suitable such area sensors (e.g., two dimensional sensors) are photodiode arrays, though sensors of various other types may also be used as desired. If, on the other hand, the portion of the cornea surface on which the incoming beam impinges at any time is not a spherical surface element with the center at the focal point 40, the reflected portion of the incident light will be reflected at an angle with respect to the incident light direction, again being redirected by the holographic element 28 and in part reflected by beam splitter 38 to impinge on the area sensor 46 at an X,Y position dependent upon the direction and extent of the nonconformance of the particular area of the cornea to the ideal theoretical spherical characteristic. Accordingly, the electrical output of sensor 46 is a measure of both the direction and extent of departure of the curvature of that local area of the cornea from the theoretical spherical contour.

In the prior description, it was assumed that the eye of the patient being examined was perfectly positioned with respect to the focal point 40 of the holographic element. Obviously, this may only be approximated, though in the preferred embodiment may in effect be continuously monitored during scanning to determine compliance with the requirement throughout the data acquisition phase of an examination. In particular, in a preferred embodiment a system of lights is used, schematically illustrated by light array 48, which may consist of a central target for the patient to focus on, an upper and lower light pair, a left and right light pair and a final fore and aft light pair. Since the holographic element 28 is in effect substantially transparent, the patient may readily see the light array 48, and accordingly may move his head up and down, left and right, and fore and aft as necessary to balance the intensity of all lights. The lights themselves are controlled by the computer based upon data gathered during the continuous scanning of the cornea. In that regard, the data taken (perhaps only a few points for alignment purposes) will clearly indicate X axis misalignment by asymmetry in the data along the horizontal, Y axis misalignment by asymmetry in the data along the vertical and Z axis (fore and aft) errors by reflection of beams incident to the cornea along lines closer to or further away from the optical axis of the system than the incident beam.

Another approach for alignment is to initially or periodically flood the eye with light rather than scanning the eye. By way of example, if the scanner is a hologon type scanner (subsequently described in greater detail), one element may spread rather than deflect the beam. An ideal cornea, perfectly positioned, will reflect all incident light along the incoming lines, resulting in sensor 46 being illuminated at a spot at the center thereof. Best alignment occurs when the spot is smallest (fore and aft position correct) and is centered on the area sensor (X and Y positions correct). Accordingly, the light array 48 will allow the patient himself to adjust the eye position for X, Y and Z location, and provide a target to maintain the center line in the desired direction.

The measurement of the Z position of the forward-most point on the cornea is also important, and should be carefully measured to provide a Z axis reference point to facilitate data reduction. In essence, this measurement provides a scale or size reference for the cornea being scanned, as the normal scan data provides local slope data not indicative of size in any absolute manner. For this purpose, in this embodiment a portion of the light beam 32 passes through beam splitter 34 to be directed along line 50 to the holographic element. This beam, being normal to the surface of the holographic element 28, is directed toward a point forward of the focal point 40, nominally the center point of the cornea of an average sized theoretically ideal eye. If, in fact, the cornea being examined is so positioned and sized, the light incident onto the cornea along line 52 is in part reflected from that surface along line 54, redirected in passing through the holographic element 28 to line 56, to be incident to the center point of a linear sensor 58. As viewed in FIG. 1, the position of the forward most point (small area) of the cornea in the Z direction toward the holographic element will cause the light incident on the linear sensor 58 to impinge thereon at a higher position on the sensor, whereas movement of the cornea away from the holographic element will caus the portion of the reflected light incident on the sensor to be incident thereon at a lower position, thereby providing the computer with continuous information with respect to the Z position of the front of the cornea. In the preferred embodiments, the source apparatus is mounted in an assembly 51 and the sensor apparatus in an assembly 57, both of which are translatable in unison toward and away from the optical axis to zero the output of sensor 58, the position of the source and sensor apparatus for zero sensor output being indicative of the position of the forward point of the cornea. This is far more accurate than merely measuring the sensor output for the Z position, as it substantially eliminates the effect of cornea size and irregularities from such reading. Finally, optical elements 53 and 59, typically single lenses, assure appropriate focus of the incident beam into the cornea, and collection of the light onto the sensor, respectively.

Figure 2:
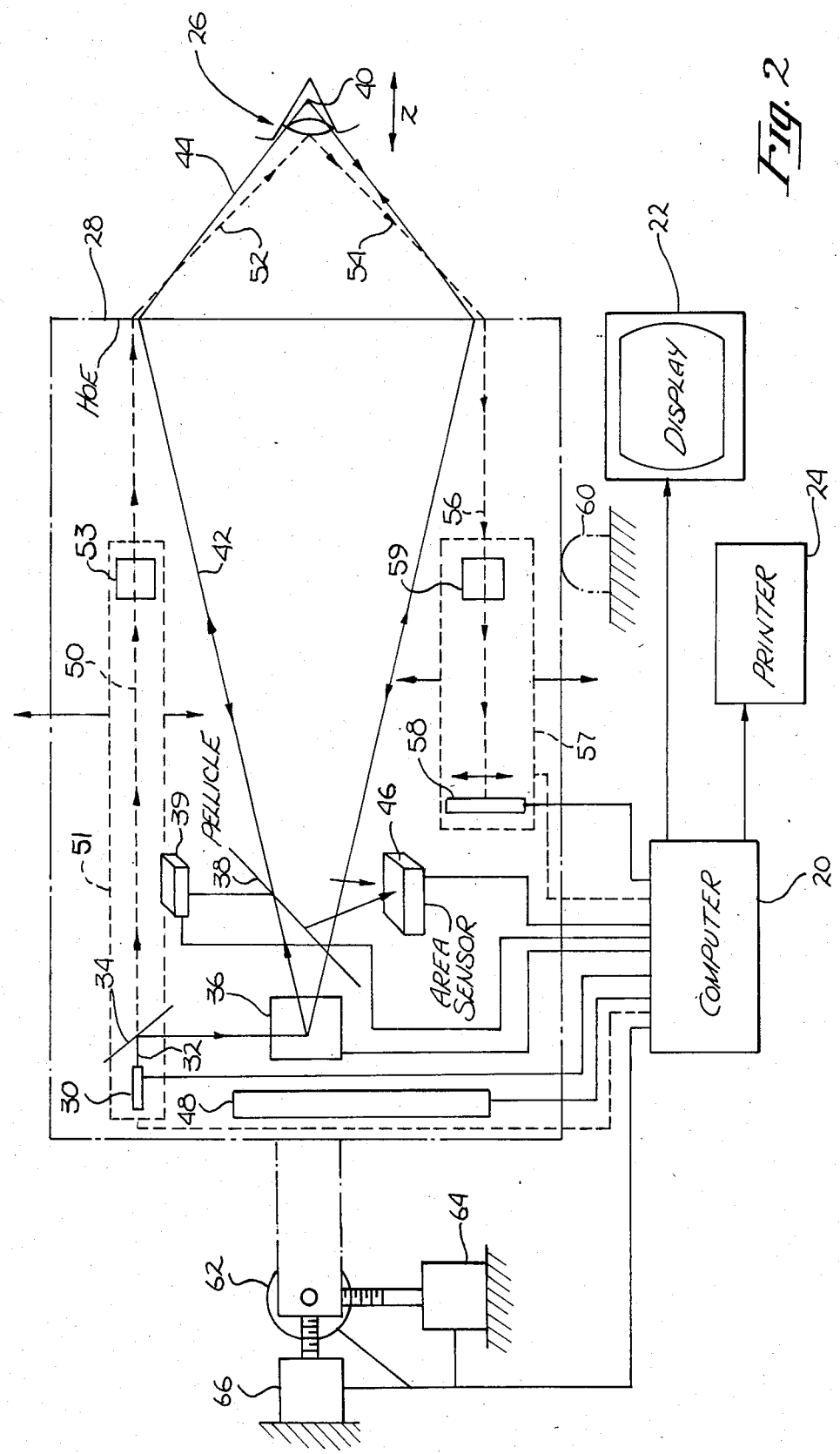
FIG. 2 is a block diagram illustrating an alternate embodiment of the present invention scanning keratometer.

Obviously, as a further alternate, the holographic element, scanner, laser, beam splitters and detectors may be mounted as part of an adjustable platform assembly under control of the computer to adjust the position of the functionable elements of the scanning keratometer with respect to the patient's eye so that relative positioning is automatic, only requiring that the patient remain still and keep the eye directed toward an appropriate visible target. This is illustrated in FIG. 2, which is a schematic diagram similar to FIG. 1, but illustrating the moveability of the scanning assembly under control of the computer 20. In particular, in this embodiment, the forward portion of the scanning assembly is mounted on the fixed frame of the keratometer, schematically represented by member 60, so as to be slideable fore and aft with respect thereto, as well as rotatable to some extent about both the X and Y axes. The other end of the assembly is shown mounted to the frame through stepper motors and lead screw assemblies 62, 64 and 66, providing adjustability at the rear of the assembly in the X, Y and Z directions for Z axis movement and X and Y axes rotations.

In such a system some form of viewable target, such as lights 48, would be presented to the patient (and/or doctor) for the patient to focus on and to lead the patient in head movement to bring the eye position into the range of the system. Thereafter, with the system operating in its usual scan mode, X, Y and Z position errors for the control of the stepper motors 62, 64 and 66 may easily be determined, as hereinbefore explained. In particular, data from one or more points a given distance or distances from the desired center of the cornea in one direction may be compared with data from one or more corresponding points the same position on the other side of the desired center of the cornea. While the correction to be applied to the appropriate stepper motor will be a nonlinear function of the difference in data between the left and right sides, a simple look-up table stored in the computer memory may easily provide the correction required based upon the data taken. Obviously, the same procedure may be used for the Y axis correction, also with the average convergence or divergence of the reflected beams indicating fore and aft or X axis errors. Thus, once within range, first order X, Y and Z corrections are readily obtained during a single scan of the cornea, which in the preferred embodiment takes approximately 1/10th of a second. Accordingly, even if a second order correction is desired, the error remaining after the first correction may be determined on a subsequent scan to provide a further fine adjustment, with the whole procedure taking only a small fraction of a second for proper alignment. Obviously, other types of automatic movement systems may also readily be incorporated and used in the described manner as desired such as, by way of example, systems which would provide translation of the scanning apparatus along any of the three axes, as the X and Y corrections may be made through the corresponding translation of the system, as opposed to the change in the direction of the optical axis thereof as in the embodiment shown schematically in FIG. 2.

In any event, once X, Y and Z axis alignments are within the desired initial alignment range, a relatively large number of scan readings are taken sequentially, typically within a fraction of a second. In that regard, something on the order of 1,000 readings may be taken in approximately 1/10 of a second, during which time the Z axis position of the cornea is repeatedly monitored. Any scan pattern desired may be used, of course, though because of the relatively large number of points and the fact that perfect alignment of the cornea is neither practical nor required, an X,Y raster-like scan is preferred.

If the patient's eye moves out of the set range during scanning the scanning is aborted and the realignment procedure is repeated. If, on the other hand, the eye remains within the set range, a number of scans, preferably at least three, are made and the data for each suitably recorded. Since in general the speed of operation of the system is normally limited to the response time of the sensor 46, as opposed to the computer speed, points on any successive scan may be compared with the corresponding point on the previous scan, so that if any points are too dissimilar, the scanning sequence will automatically abort, whereby realignment may be reestablished. If, on the other hand, all points fall within a preset range, then slope errors may be computed and a topographic representation of the eye prepared and presented on the display and/or printed out in any form desired. In that regard, the allowed measure of the dissimilarity between points in successive scans may be substantially different from and in particular, smaller than the corresponding measure of initial alignment of the cornea, as cornea alignment is primarily intended to assure that the equipment is operating well within its preestablished operating range, whereas the dissimilarity of successive data points indicates cornea movement during data acquisition which movement, even if totally within the allowable initial cornea position, will directly cause errors in the data.

As previously described, the light source 30 preferably is a low power HeNe laser, though other light sources may readily be used provided they are reasonably monochromatic to assure performance of the holographic element within the required limits. The beam splitters 34 and 38 may be of standard construction, partially silvered mirrors being entirely suitable for such purpose. The scanner 36, on the other hand, may take various forms, each having various advantages in the particular system. By way of example, the scanner 36 may be a pair of single axis or a double axis voice coil scanners, e.g., voice coil drivers driving one or more mirrors in angular deflection. Such scanners have the advantage of relatively low cost, and have an adequate frequency response for the application. In that regard, scanner position accuracy is not overly critical in this application, as cornea deviations from the spherical ideal are gradual so that a scanner position error of one or two percent will give rise to only a very small error in any reading. Similarly, a piezoelectric driven scanner may also be used, all of the foregoing types of scanners being driven through the desired scanning pattern or servoed through the desired scanning pattern by the computer.

Another form of scanner which is of interest for use with the present invention is the hologon. Such a scanner utilizes a rotating member through which the monochromatic beam is directed, the rotating member successively bringing different holographic elements or different portions of a single holographic element, each having its own characteristics, into alignment with the beam so as to successively deflect the beam in accordance with the characteristics of each such element or element portion. Such a scanner has certain advantages in the present invention, as it may in effect step the beam from point to point in the scan pattern independent of the dynamic response of an open loop or servoed conventional mechanical scanner. A single such rotating disk could be used to induce the X and Y deflection, though a rather large number of elements on the disk would be required. Preferably a pair of such disks is used to rotate at cooperative speeds to provide a raster scan-like X, Y sweep of the scan area. One could, if desired, sweep the scan area out of sequence, or perhaps repeat certain scan lines a number of times throughout a given cornea scan, such as repeating scan lines substantially up from and down from the center of the cornea, which two lines could be used during data reduction to provide a first order estimate of and correction for X, Y and Z axis motion of the eye during the cornea area scan (data acquisition) phase. Similarly flooding the eye with light periodically during the scan will also provide data from which eye movement can be calculated for data correction purposes.

There has been described herein new forms of scanning keratometers which have the advantages of speed, ease of use, accuracy and low cost. While the invention has been described in the general context of diagnostic examinations, the invention may also be used during ophthalmic surgical procedures such as cataract surgery, radial keratotomy, etc., to monitor the condition of the cornea. In that regard, its use is not limited to that of a conventional keratometer, but may also be used for other purposes, such as, by way of example, to measure and/or monitor width and depth of incisions made by diamond knife or laser during radial keratotomy. Also, while preferred embodiments have been disclosed and described herein, it will be obvious to those skilled in the art that various changes in form and detail may be made therein without departing from the spirit and scope of the invention.

We claim:

1. A scanning keratometer comprising
light source means for providing a beam of substantially monochromatic light;
deflection means for deflecting the light beam from said light source means in a predetermined pattern;
a holographic element positioned for focusing monochromatic light incident to a first face of said holographic element from said light source and deflection means toward a fixed first focal point spaced outward from the second face of said holographic element, and for receiving monochromatic light reflected by the surface of the cornea of an eye positioned with its center approximately at said first focal point; and
sensing means positioned for sensing the relative position of the portion of a light beam directed toward said fixed focal point and reflected back through said holographic element by the surface of the cornea of an eye positioned with its center approximately at said first focal point.

2. The scanning keratometer of claim 1 wherein said sensing means comprises a beam splitter and a two dimensional light sensor, said beam splitter being positioned between said deflection means and said holographic element to deflect light returning from said holographic element to said light sensor, said light sensor being positioned so that the approximate center thereof is positioned at a second focal point, said second focal point being the focal point for light reflected from a cornea along any little through said first focal point, whereby the output of said sensing means will be indicative of the direction and extent of deviation of the local area of the cornea illuminated by the light beam from a true spherical segment having its center at said first focal point.

3. The scanning keratometer of claim 1 further comprised of visual alignment means viewable through said second face of said holographic element, said visual alignment means being a means for guiding the patient in eye movement to align the eye in a plane parallel with said holographic element for X, Y and Z alignment of the center of the eye with said first focal point.

4. The scanning keratometer of claim 3 further comprised of computer means coupled to said deflection means and said sensing means for recording the output of said sensing means at predetermined positions of said deflection means.

5. The scanning keratometer of claim 4 further comprised of a second sensor and beam directing means, said beam directing means being a means for directing, a portion of said light from said light source toward said holographic element, to be defracted thereby to be incident upon the forward region of the cornea of an eye positioned with its center at said first focal point, said second sensor being positioned to intercept light reflected from the forward most region of the cornea of an eye positioned at said first focal point and again defracted by said holographic element, whereby the output of said second sensor will be indicative of the Z distance of the front of said cornea from said first focal point toward said holographic element.

6. The scanning keratometer of claim 5 further comprising computer means coupled to said deflection means and said sensing means for recording the output of said sensing means at predetermined positions of said deflection means wherein said second sensor is coupled to said computer means for providing a signal thereto indicative of Z distance alignment of a cornea to be scanned.

7. The scanning keratometer of claim 6 wherein said beam directing means and said second sensor may move in translation toward and away from the optical axis of said scanning keratometer in response to the output of said second sensor.

8. The scanning keratometer of claim 1 wherein said light source, deflection means, holographic element and sensing means comprise a moveable assembly, and further comprising a stationary frame assembly and drive means, said moveable assembly being mounted on said stationary frame assembly for movement with respect thereto, said drive means being coupled between said stationary frame assembly and said moveable assembly, and further being coupled to a computer means, said drive means being responsive to signals provided thereto from said computer means to position said moveable assembly in response thereto, whereby once the eye of the patient is approximately positioned, the output of said sensing means and may be used to control said drive means to accurately position said moveable assembly with respect to the eye to be scanned prior to recording the output of said sensing means at predetermined positions of said deflection means.

9. The scanning keratometer of claim 1 further comprising of computer means coupled to said deflection means and said sensing means for recording the output of said sensing means at predetermined positions of said deflection means.

10. The scanning keratometer of claim 1 wherein said light source is a low power laser light source.

11. The scanning keratometer of claim 1 wherein said deflection means comprises a hologon.

12. The scanning keratometer of claim wherein said deflection means comprises a pair of hologons rotating at cooperative speeds, whereby one hologon may cause deflection of said beam in a first direction and the the second hologon may cause deflection of said beam in a second direction.

13. The scanning keratometer of claim 1 further comprised of means for flooding a cornea with light from said light source, whereby the position and size of the spot of reflected light on said sensor may be used as indicative of X, Y and Z position errors.

14. The scanning keratometer of claim 1 further comprised of second sensor means for measuring the beam deflection caused by said deflection means.

15. A scanning keratometer comprising
a laser light source for providing a beam of substantially monochromatic light;

a double axis deflection means for deflecting the light beam from said light source means in a predetermined pattern;

a holographic element positioned for focusing monochromatic light incident to a first face thereof from said light source and deflection means toward a fixed first focal point spaced outward from the second face thereof, and for receiving monochromatic light reflected by the surface of the cornea of an eye positioned with its center approximately at said first focal point;

sensing means positioned for sensing the relative position of the portion of a light beam directed toward said fixed focal point and reflected back through said holographic element by the surface of the cornea of an eye positioned with its center approximately at said first focal point; and computer means coupled to said deflection means and said sensing means for recording the output of said sensing means at predetermined positions of said deflection means.

16. The scanning keratometer of claim 15 wherein said sensing means comprises a beam splitter and a two dimensional light sensor, said beam splitter being positioned between said deflection means and said holographic element to deflect light returning from said holographic element to s id light sensor, said light sensor being positioned so that the approximate center thereof is positioned at a second focal point, said second focal point being the focal point for light reflected from a cornea along any line through said first focal point, whereby the output of said sensing means will be indicative of the direction and extent of deviation of the local area of the cornea illuminated by the light beam from a true spherical segment having its center at said first focal point.

17. The scanning keratometer of claim 15 wherein said light source, deflection means, holographic element and sensing means comprise a moveable assembly, and further comprising a stationary frame assembly and drive means, said moveable assembly being mounted on said stationary frame assembly for movement with respect thereto, said drive means being coupled between said stationary frame assembly and said moveable assembly, and further being coupled to said computer means, said drive means being responsive to signals provided thereto from said computer means to position said moveable assembly in response thereto, whereby once the eye of the patient is approximately positioned, the output of said sensing means may be used to control said drive means to accurately position said moveable assembly with respect to the eye to be scanned prior to recording the output of said sensing means at predetermined positions of said deflection means.

18. The scanning keratometer of claim 17 further comprised of visual alignment means viewable through said second face of said holographic element, said visual alignment means being a means for guiding the patient in eye movement to align the eye for X, Y and Z alignment of the center of the eye with said first focal point.

19. The scanning keratometer of claim 17 further comprised of a second sensor, a portion of said light from said light source being directed toward said holographic element to be defracted thereby to be incident upon the forward region of the cornea of an eye positioned with its center at said first focal point, said second sensor being positioned to intercept light reflected from the forward most region of the cornea of an eye positioned at said first focal point and again defracted by said holographic element, whereby said second sensor will be indicative of the Z distance of the front of said cornea.

* * * * *

UNITED STATES PATENT AND TRADEMARK OFFICE
CERTIFICATE OF CORRECTION

PATENT NO. : 4,662,730

DATED : 5/5/87

INVENTOR(S) : OUTWATER ET AL.

It is certified that error appears in the above-identified patent and that said Letters Patent is hereby corrected as shown below:

| COLUMN | LINE | DESCRIPTION |
|--------|------|-------------|
| 4 | 32 | delete "caus" insert --cause-- |
| 9 | 28 | delete "s id" insert --said-- |

Signed and Sealed this

Sixth Day of September, 1988

Attest:

DONALD J. QUIGG

Attesting Officer

Commissioner of Patents and Trademarks